United States Patent [19]  [11] 4,054,522
Pinkerton  [45] Oct. 18, 1977

[54] APPARATUS FOR EXPOSING A FLUID TO A NEGATIVE PRESSURE

[76] Inventor: Harry Pinkerton, Bridle Path Lane, Mill Neck, N.Y. 11765

[21] Appl. No.: 687,263

[22] Filed: May 17, 1976

Related U.S. Application Data

[63] Continuation-in-part of Ser. No. 610,037, Sept. 3, 1975, abandoned.

[51] Int. Cl.$^2$ .............................................. B01D 19/00
[52] U.S. Cl. .................... 210/188; 210/321 B; 137/99
[58] Field of Search ............... 210/96 M, 321 B, 188, 210/436, 22; 55/163; 417/391, 393, 394, 395, 250; 137/99, 101.21

[56] References Cited

U.S. PATENT DOCUMENTS

| | | | |
|---|---|---|---|
| 3,091,186 | 5/1963 | Hofmeister et al. | 417/250 |
| 3,598,727 | 8/1971 | Willock | 210/321 B |
| 3,672,389 | 6/1972 | McConnell et al. | 137/99 |
| 3,825,122 | 7/1974 | Taylor | 210/137 |
| 3,976,574 | 8/1976 | White | 210/321 A |

OTHER PUBLICATIONS

C. Cheng et al., "A flow Work Exchange for Desalination Processes," Oct. 1968, pp. 48, 50-51, Research Dev. Report.

Primary Examiner—Frank A. Spear, Jr.
Assistant Examiner—E. Rollins Cross
Attorney, Agent, or Firm—Nolte and Nolte

[57] ABSTRACT

Apparatus for exposing a fluid to a negative pressure particularly for degassing liquid containing a gas comprises a double acting piston/cylinder unit of which the cylinder is divided into two chambers by the piston, the volume of one chamber swept by the piston being lesser than that swept by the piston in the other chamber. An inlet for a fluid is made to said one chamber, a conduit connects the two chambers and an outlet is made from the other chamber. Valve means are associated with the conduits to permit controlled reciprocation of the piston within the cylinder and fluid passed from said one chamber to the other is exposed to a negative pressure in the other chamber, gas, in the situation in which the fluid is a gas-containing liquid, forming bubbles in the other chamber or, where the fluid is wholly liquid, a part of that liquid being vaporized. The contents of the other chamber are then passed through the outlet from the other chamber to, where the fluid is a gas-containing liquid, a bubble trap in which the gas is separated from the liquid or, where the fluid is wholly liquid, the gaseous phase or vapor will be condensed upon release of pressure and moved through the outlet to be used as required. In a variation the piston/cylinder structure is replaced by a simple receptacle provided with a flexible diaphragm.

23 Claims, 5 Drawing Figures

APPARATUS FOR EXPOSING A FLUID TO A NEGATIVE PRESSURE

REFERENCE TO RELATED APPLICATIONS

This application is a continuation-in-part of application Ser. No. 610,037 filed Sept. 3, 1975, now abandoned.

BACKGROUND OF THE INVENTION

This invention is concerned with apparatus for exposing a fluid to a negative pressure. There are many instances in which it is necessary to remove gas from a liquid where the gas is carried in the liquid either in solution or is finely dispersed throughout the liquid. One such instance is in the liquids used in hemodialysis processes. In these processes, conventionally water is mixed with a dialysate concentrate to form a dialysate solution and that solution is then caused to pass to one side of a membrane of a dialysis cell, wastes from blood passing the other side of the membrane being drawn across that membrane.

It is well known that it is extremely important to monitor the quantity of wastes withdrawn from the blood of a patient and the rate at which those wastes are drawn. It is further well known that a major source of error in attempts to monitor these parameters has been the inclusion of gases in the liquids utilized in the procedure and various techniques have been adopted either to compensate for the presence of gas or to remove gas from the liquids.

The present invention seeks to provide a simple and effective apparatus which is effective to degas a liquid, that apparatus being particularly, but not exclusively, useful for degassing liquids utilized in hemodialysis procedures.

There are also processes in which it is required to subject a liquid to a negative pressure as, for example, in scientific processes employing dehiscent particle activation to initiate localized reactions.

The present invention also provides apparatus effective for this purpose.

BRIEF SUMMARY OF THE INVENTION

Basically according to this invention, there is provided an apparatus for subjecting a fluid to a negative pressure which comprises a receptacle with a partition reciprocable therein and dividing the cylinder into two chambers. The partition is arranged, preferably by having a rod projecting from one side thereof and extending through an end wall of the receptacle, to sweep a lesser volume in one of those chambers than is swept in the other chamber. A fluid, which may be wholly liquid or a liquid having gas entrained therein, is admitted to the smaller volume chamber as that chamber expands and is delivered from the smaller volume chamber to the larger volume chamber as the larger chamber expands and, of course, the fluid is exposed to a negative pressure in the larger chamber because of the difference in volume between the amount of fluid moved from the smaller chamber and the volume of the larger chamber to be filled. If the fluid is wholly liquid, then evaporation will occur to accommodate the difference in volume or, if the fluid is a gas-containing liquid, the gas will form bubbles. As the partition reverses and moves to expand the smaller volume chamber, so the fluid is moved out of the larger volume chamber to, when the fluid is a gas-containing liquid, a separating means, such as a bubble trap, where the gas is vented or, where the fluid is wholly liquid, that vapor will be condensed as the negative pressure is removed.

Most desirably, when the fluid is a gas-containing liquid the outlet for the liquid and gas bubbles is disposed in an upper region of the larger chamber of the receptacle to insure that the lighter gas all passes from that chamber. Most desirably, in this instance, the receptacle which may be a cylinder is mounted generally horizontally and to be pivotable in a vertical plane so that it rocks as the center of gravity of the unit moves to either side of the pivot with movement of the partition. In this way the bubbles are constrained under the influence of gravity to move towards the outlet of the larger chamber, that outlet being disposed in an upper region of the cylinder.

While hereabove the expressions gas "entrained" in liquid or "gas-containing liquid" have been utilized, it is to be appreciated that these expressions are intended to be generic to gas which is in solution in the liquid and to that situation in which the gas is finely dispersed throughout the liquid. The expressions are used in this sense hereinafter.

BRIEF DESCRIPTION OF THE DRAWINGS

Embodiments of the invention are illustrated in the accompanying drawings, in which.

DESCRIPTION OF THE PREFERRED EMBODIMENTS

Figure 1:
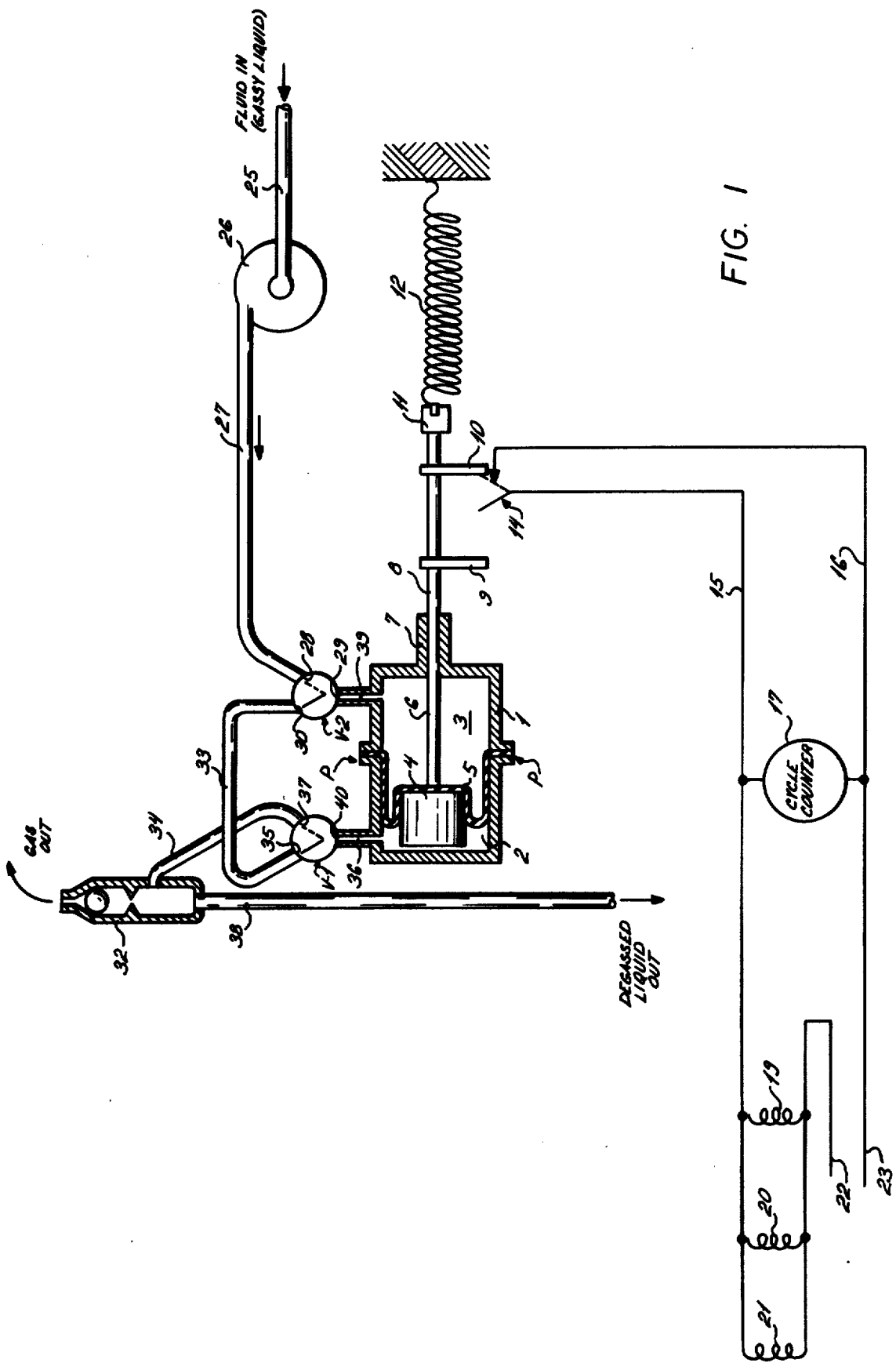
FIG. 1 is a simplified and schematic illustration of a degassing unit according to this invention.

The apparatus of FIG. 1 comprises a piston/cylinder unit 1 which is divided into chambers 2 and 3 by piston 4 which has a rolling diaphragm 5. Extending from one end of the piston is a piston rod 6 guided in an extension 7 of an end wall of the cylinder.

The region 8 of the piston rod outside of cylinder 1 is provided with adjustable stop means 9 and 10 which cooperate, in a manner to be described hereinafter, with a switch indicated generally at 14. Secured to the end of the piston rod at 11 is a spring 12, the other end of that spring being fixed so that the spring is effective to bias the piston from left to right.

The switch 14 is included in a circuit 15, 16 which comprises, optionally, a cycle counter 17 and coils 19 and 20 of solenoids associated with valves (described hereinafter) and motor 21 which drives a pump 26. A connection to an electrical supply is made at terminals 22 and 23.

An inlet 25 for a gas-containing liquid is made through centrifugal pump 26 to line 27. While in the specific embodiment of the invention illustrated in the drawings, a centrifugal pump 26 is utilized, it must be appreciated that any source of pressurized fluid could be effective or that a mechanical or electrical drive could be applied to the piston. Line 27 extends to inlet port 28 in a three port valve V-2, through said valve V-2 to common valve port 29 which is connected to inlet port 39 of the cylinder which leads to chamber 3 of cylinder 1.

A connection is made between chamber 3 of cylinder 1 and chamber 2 by means of cylinder port 39 and valve port 29, through the third port 30 in valve V-2 and via line 33 to inlet port 35 of a three port valve V-1. The connection is completed from inlet port 35, to common port 40 of valve V-1 and to cylinder port 36 which enters chamber 2 of cylinder 1.

Cylinder port 36, besides serving as an inlet for fluid from chamber 3 to chamber 2, serves also as an outlet from chamber 2, the outlet being made from common port 40 of valve V-1 to port 37 from which line 34 leads to a bubble trap 32, that bubble trap being of conventional form having a ball valve controlling a gas outlet at the upper end of the trap and a liquid outlet 38 at its lower end.

As indicated schematically at P, the cylinder is mounted in a frame, together with the drive mechanism associated therewith for pivotal movement about a horizontal axis, the arrangement being such that with movement of the piston the center of gravity of the assembly shifts from one side to the other of the pivot axis so that the assembly tilts. It is to be appreciated that, by the utilization of a flexible drive connection and by the replacement of the switching mechanism, for example by proximity switches operable by the piston, it may be possible simply to pivot the cylinder within a frame and have the frame itself fixed.

The operation of the device is as follows. At the completion of right to left movement of the piston the switch 14 will be thrown by the adjustable stop 10 to break the electrical supply to motor 21 and interrupt the operation of pump 26. At the same time, valves V-1 and V-2, controlled by solenoids 19 and 20, will be moved to the positions indicated in full line. Upon interruption of the supply of motive fluid from pump 26, the piston 4 will begin to move left to right under the influence of spring 12 and the liquid and gas entrained therein will pass from cylinder port 39, through ports 29 and 30 of valve V-2 and into connecting line 33. From line 33 the liquid will pass from port 35 to port 40 of valve V-1 then through cylinder port 36 to chamber 2. Since the effective volume of chamber 2 is greater than that of chamber 3 (because of the volume of chamber 3 occupied by piston rod 6) the gas entrained in the liquid which moves into chamber 2 must expand to fill the space and will form bubbles in chamber 2.

As the piston completes its left to right movement, adjustable stop 9 will throw switch 14 to complete the circuit to motor 21 driving pump 26 and to the solenoids 19 and 20 to cause valves V-1 and V-2 to be thrown to the positions indicated in chain line. At this time, liquid from the pump will enter chamber 3 through ports 28 and 29 of valve V-2 and will move the piston right to left against the action of spring 12. Simultaneously, the liquid and gas bubbles in chamber 2 will be moved through cylinder port 36 via ports 40 and 37 of valve V-1 to the bubble trap 32 from which the gas will vent to atmosphere and the liquid will pass through outlet 38 to be utilized as required.

It will be appreciated that as the piston makes its left to right movement, bubbles will be forming in chamber 2 and that as the piston moves to a position in which the center of gravity is to that side of the pivot at the right as viewed in FIG. 1, so the left hand end of the cylinder will be in an uppermost position and the bubbles will be immediately adjacent cylinder port 36 so that as the piston reverses and begins its right to left movement, the bubbles will be forced from chamber 2 to the bubble trap before the cylinder tilts to move the left hand side of the cylinder downwards.

Figure 2:
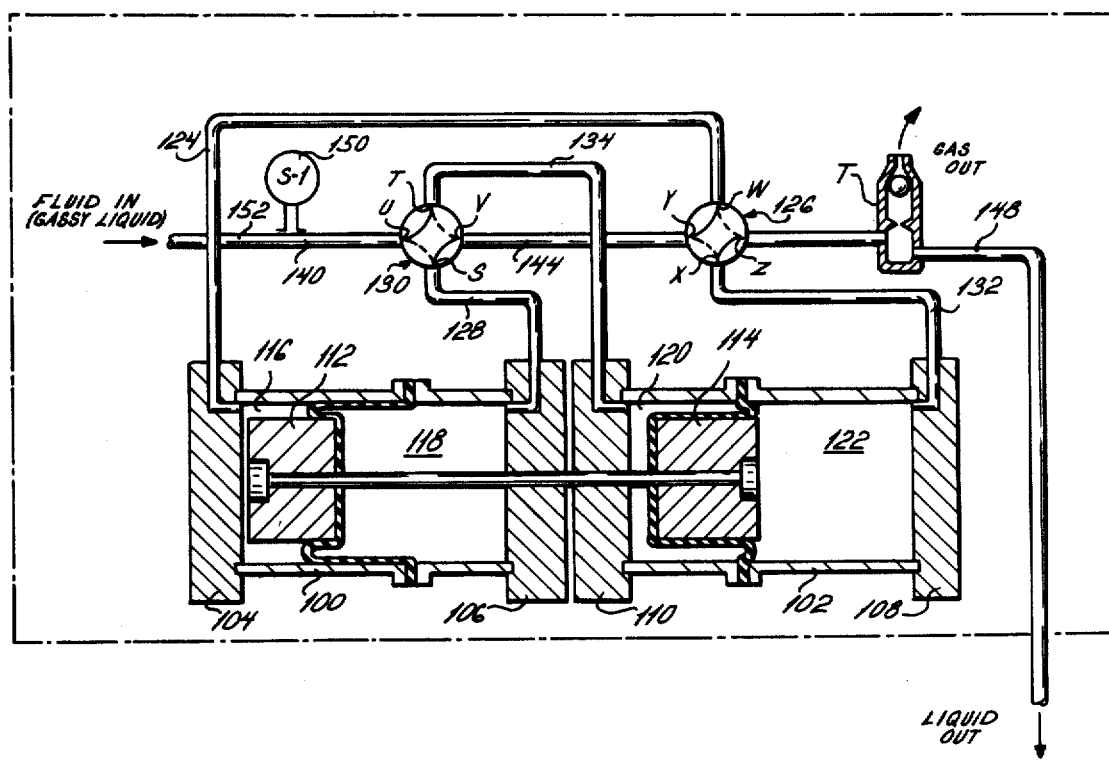
FIG. 2 shows schematically a duplex version of the invention.

A duplex version of the system is illustrated in FIG. 2. In that arrangement, there are two piston/cylinder units arranged end to end in co-axial relationship. Many of the component parts of the apparatus illustrated in FIG. 2 are similar to those of FIG. 1, however, in the interests of clarity, the parts of the apparatus of FIG. 2 are identified by different reference numerals than those utilized in the embodiment of FIG. 1.

The apparatus of FIG. 2 comprises a left hand cylinder 100 and a right hand cylinder 102. The ends of cylinder 100 are closed by port plate 104 and 106 and those of cylinder 102 are closed by port plates 108 and 110. Disposed within cylinders 100 and 102 are pistons 112, 114, respectively, each provided with a conventional rolling diaphragm seal so that cylinder 100 is divided into chambers 116 and 118 at opposite ends of the piston 112 and cylinder 102 is divided into chambers 120 and 122 at opposite ends of piston 114. It is to be noted that the pistons are joined by a common piston rod sliding in port plates 106 and 110, that piston rod being effective to render the effective volume of chamber 118 lesser than that of chamber 116 and the effective volume of chamber 120 lesser than that of chamber 122.

Leading from chamber 116 to port plate 104, conduit means 124 communicates with port W of a four port valve 126 and conduit 128 leads to port S of a four port valve 130 from chamber 118 through port plate 106. Conduit 132 leads to port X of valve 126 from chamber 122 through port plate 108 and conduit 134 communicates between chamber 120 and port T of valve 130.

An inlet conduit 140 for a gas-containing liquid leads to port U of valve 130 and includes a pressure responsive switch S-1. Conduit 144 connects port V of valve 130 with port Y of valve 126.

Valve 126 also includes a port Z which leads to an outlet conduit 148 which includes a bubble trap T of conventional form including an upper, ball controlled, gas outlet and a lower liquid outlet.

Disposed in branch 152 of the inlet 140, to be exposed to pressure in the inlet, is a pressure responsive switch 150 the operation of which is described in detail hereinafter.

The apparatus of FIG. 2 operates basically as follows: in the position of the valve shown in full line, liquid-containing gas is admitted via ports U and T of valve 130 to conduit 134 and thence to chamber 120, causing the pistons 112 and 114 to begin left to right movement. The liquid and bubbles in chamber 122 (the production of which is described hereinafter) are then moved to a conduit 132, through ports X and Z of valve 126 and to the bubble trap T, the gas issuing from the upper gas outlet thereof and the liquid being delivered to outlet conduit 148.

At the same time, the gas-containing liquid in chamber 118 passes along conduit 128, through ports S and V of valve 130 and ports Y and W of valve 126 to conduit 124 and then to chamber 116. Since the volume of chamber 116 is greater than that of chamber 118, gas entrained in the liquid will form bubbles and separate from the liquid.

The left to right movement of the pistons is completed when piston 112 contacts port plate 106 causing fluid pressure build up in fluid inlet line 152 and on pressure responsive switch 150 which will be operated to shift the valves to the positions shown in chain dot line at which time the gas-containing liquid will be admitted via ports U and S of valve 130 to chamber 118, causing the pistons to commence their right to left movement and causing the gas and bubbles in chamber 116 to be moved through conduit 124 and ports W and Z of valve 126, to the gas trap T from which the gas will be vented and the liquid passed to outlet conduit 148. At the same time, the gas-containing liquid in chamber 120 will be moved along conduit 134 through ports T and V of valve 130 along conduit 144 through ports Y and X of valve 126 and along conduit 132, to chamber 122. Since, of course, the volume of chamber 122 is greater than that of chamber 120, the gas contained in the liquid will form bubbles to be moved from the chamber at the next cycle.

It will be appreciated that with the embodiment here described a convenient motive force for the pistons is pressurized liquid admitted thereto along the liquid inlet line leading to port U of valve 130, however, it is to be understood that other motive forces may be utilized as, for example, a suction pressure on line 148, or a magnetic drive could be used or a direct mechanical drive with appropriate modifications in the various connections.

Figure 3:
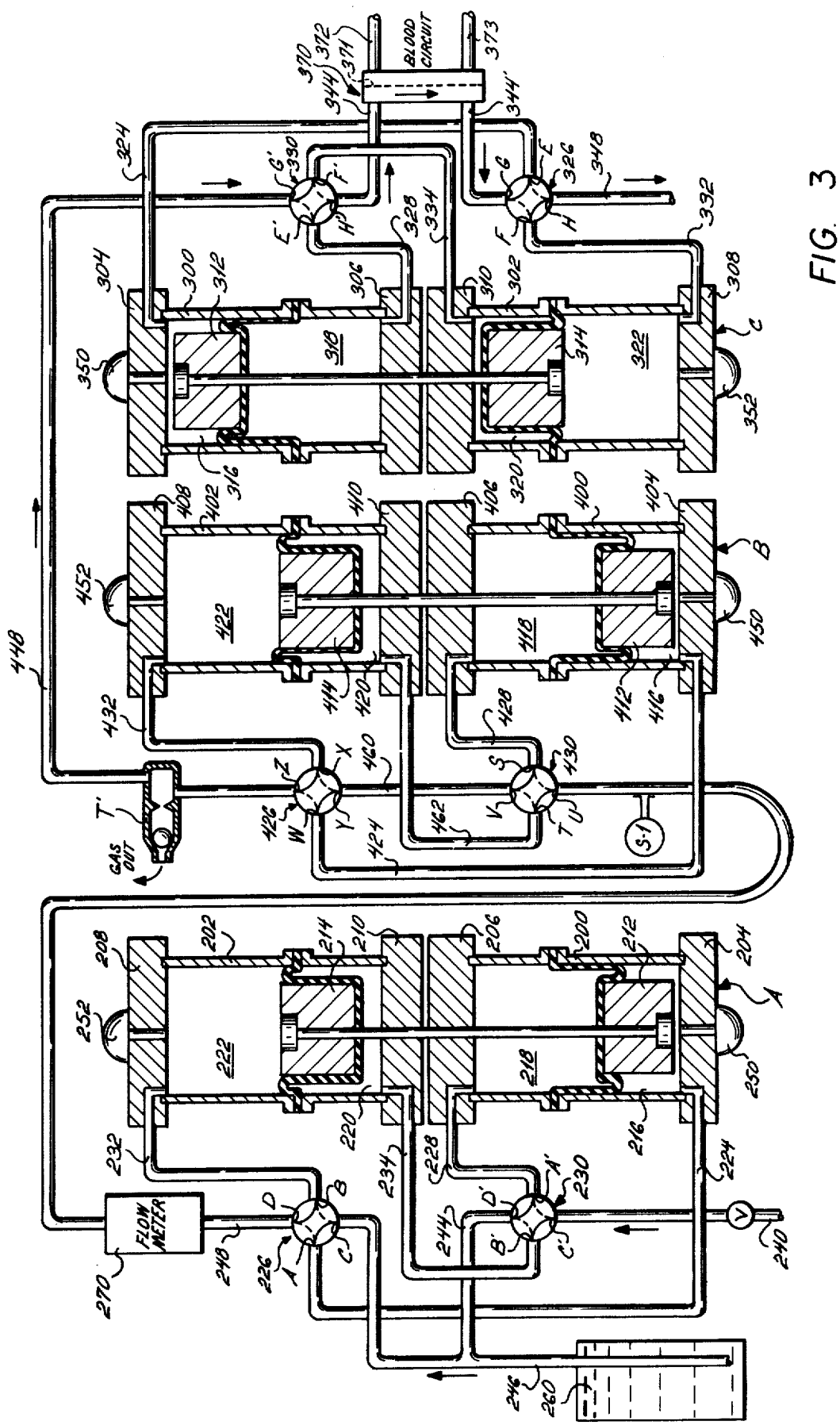
FIG. 3 shows, schematically, how the system of the present invention may be incorporated in apparatus for utilization in a hemodialysis procedure.

The equipment illustrated schematically in FIG. 3 is utilized in a dialysis procedure and comprises double acting piston and cylinder units indicated generally at A, B and C, unit A serving to mix dialysate concentrate and water to produce a dialysate solution which is delivered to unit B. Unit B is effective to degas the dialysate solution in accordance with the teachings of the present invention and unit C is effective to deliver the degassed dialysate solution to hemodialysis cell 370 and to control the rate of withdrawal of blood wastes from blood admitted to the blood side of cell 370.

It is to be appreciated that while the piston/cylinder units are oriented on the drawing as being in a vertical position, they would, in fact, most usually be disposed horizontally and that where the adjectives "upper" and "lower" are used hereinafter to describe the pistons and cylinders of the individual units, in fact those adjectives are used exclusively with regard to the relationship of the various parts on the drawings and not necessarily to the relationship which those parts would have in operation.

Unit A comprises a lower cylinder 200 and an upper cylinder 202, the ends of cylinder 200 being closed by port plates 204 and 206 and those of cylinder 202 being closed by port plates 208 and 210. Disposed within cylinders 200 and 202 are pistons 212 and 214, respectively, each provided with a conventional rolling diaphragm seal so that cylinder 200 is divided into chambers 216 and 218 at opposite ends of the piston 212 and cylinder 202 is divided into chambers 220 and 222 at each end of piston 214. The pistons are joined by a common piston rod guided in port plates 206 and 210.

From chamber 216 a conduit 224 leads to port A of a four valve 226 and conduit 228 leads to port A' of four port valve 230, from chamber 218.

Conduit 232 leads to port B of valve 226 from chamber 222 and conduit 234 communicates between chamber 220 of cylinder 202 and port B' of valve 230.

A pressurized water inlet conduit 240 is connected to port C' of valve 230 and conduit 244 communicates between port D' of valve 230 and port C of valve 226, conduit 244 including a T having a branch 246 communicating with a source of a dialysate concentrate 260. The port plates 204 and 208 are provided with proximity switches 250 and 252, respectively, or there may be provided a pressure responsive switch as described supra with respect to the embodiment of FIG. 2.

The apparatus thus far described is effective to provide a precise mixture of diluting water and a dialysate concentrate and effectively to mix those two components to form a dialysate solution.

The operation of the device is as follows:

Diluting water is admitted along conduit 240 and through ports C' and B' of valve 230, to chamber 220 of cylinder 202 causing the pistons to begin their upward movement. During this movement, liquid contained in chamber 222 passes along conduit 232 and via ports B and D of valve 226 to a flow meter 270 thence further along the circuit.

Also during upward movement, the liquid contained in chamber 218 is caused to move along conduit 228 through ports A' and D' of valve 230, along conduit 244 through ports C and A of valve 226 and into chamber 216 via conduit 224. Since the volume of chamber 216 is greater than that of 218, because of the presence of the piston rod interconnecting the pistons, a guantity of concentrate from supply 260 will be drawn along conduit 246 to mix thoroughly with the water passing along conduit 244 and conduit 224, that quantity being directly related to the cross sectional area of the piston rod multiplied by the stroke of the piston.

As the pistons complete their upward stroke, proximity switch 252 will be operated to cause the valve 226 and 230 to be shifted to their chain line position at which time water will be delivered to chamber 218 along conduits 240 and 228 via ports C' and A' of valve 230, causing the pistons to begin their downward movements. The mixed solution in chamber 216 will be forced during this movement along conduit 224 to valve 226 and through ports A and D of that valve to conduit 248, through flow meter 270 thence to pass further along the circuit.

Simultaneously, the water previously admitted to chamber 220 will be passed along conduit 234 to conduit 244 through valves B' and D' of valve 230 and, through ports C and B of valve 226 and conduit 232, into chamber 222. Again, since the volume of chamber 222 is greater than that of chamber 220, a quantity of the concentrate from supply 260 will be drawn into conduit 244 to mix with the water from chamber 220 and to be admitted to chamber 222, the quantity of concentrate again being dictated by the cross sectional area of the piston rod multiplied by the stroke of the piston. As cycling continues, so precisely mixed solution will be passed from unit A along the connection to valve 430 of unit B.

Unit B comprises a lower cylinder 400 and an upper cylinder 402, the ends of cylinder 400 are closed by port plates 404 and 406 and those of cylinder 402 are closed by port plates 408 and 410. Disposed within cylinders 400 and 402 are pistons 412 and 414, respectively, with the piston 412 dividing cylinder 400 into chambers 416 and 418 and piston 414 dividing cylinder 402 into chambers 420 and 422. The pistons 412 and 414 are connected by a common piston rod extending through appropriate guide apertures in port plates 406 and 410. Proximity switches 450 and 452 are provided in port plates 404 and 408, respectively but again, those switches may be replaced by a pressure responsive switch operating as described with reference to FIG. 2 hereabove.

A conduit 424 connects 416 of cylinder 400 with port W of valve 426; conduit 428 connects chamber 418 with port S of valve 430; conduit 460 connects port V of valve 430 with port Y of valve 426; conduit 462 connects chamber 420 of cylinder 402 with port T of valve 430 and conduit 432 connects chamber 422 of cylinder 402 with port X of valve 426. An outlet 448 from port Z of valve 426 leads to a bubble trap T' and then to unit C as described hereinafter.

The operation of unit B is substantially as follows: the dialysate solution delivered from unit A reaches valve 430 and, with the valves in the position shown in full line moves via ports U and T to conduit 462 to be admitted beneath piston 414 causing the pistons to begin their upward movement. At the same time, solution previously admitted to chamber 418 passes along conduit 428 to ports S and V of valve 430, along conduit 460 and, via ports Y and W of valve 426 and conduit 424, to chamber 416 of cylinder 400. The solution in chamber 418 includes entrained gas, that gas generally being in solution, and as it passes to chamber 416, since chamber 416 is of larger volume than chamber 418, the gas will come out of solution and form bubbles to occupy the greater space of chamber 416.

As the pistons complete their upward movement, proximity switch 452 will be operated causing valves 426 and 430 to be thrown to the positions indicated in chain line. At this time, the fluid delivered from unit A will pass through ports U and S of valve 430 along conduit 428 to chamber 418 of cylinder 400 causing the pistons to move downwardly. The bubbles and liquid in chamber 416 will then be moved along conduit 424 through ports W and Z of valve 426 to the bubble trap T' where the gas will exit to atmosphere and the degassed solution will be moved into conduit 448.

Simultaneously, the solution containing dissolved gas previously admitted to chamber 420 will be moved from that chamber along conduit 462, through ports T and V of valve 430, to conduit 460. The solution will then pass through ports Y and X of valve 426, along conduit 432 and into chamber 422 of cylinder 402. Since the volume of chamber 422 is greater than that of chamber 420, the gas and solution in that chamber will come out of solution and form bubbles to occupy the greater space.

As cycling continues, so the liquid reaching conduit 448 will be degassed and that liquid will continue into C.

The piston/cylinder unit C is of itself structurally similar to units A and B, the primary difference being in the connections between the valves associated with that unit and the dialysis cell. As such, its particular structure is not described in detail.

The connections in unit C are between lower chamber 322 of cylinder 302, via conduit 332 and port F of valve 326. A conduit extends between port G of valve 326 and the solution side of dialysis cell 370 which is divided into a solution side and a blood side by membrane 371. The cell is entirely conventional.

Conduit 334 extends between chamber 320 of cylinder 302 and port F' of valve 330 and conduit 344 extends between port H' of valve 330 and the solution side of the cell 370.

A conduit 324 extends between chamber 316 of cylinder 300 and port E of valve 326; conduit 328 extends between chamber 318 of cylinder 300 and port E' of valve 330. The connection 448 between units B and C connects to ports G' of valve 330 and an exhaust line 348 leads from port H of valve 326, to waste.

Conventional conduits 372 and 373 are connected from the blood side of the cell 370 to a patient.

Degassed dialysate solution from unit B enters port G' of valve 330 and passes through port F' to chamber 320 of the cylinder 302, causing the pistons 312 and 314 to begin their downward movement. During this movement the liquid in chamber 322 which comprises blood wastes and solution, passes along line 332 and, via conduits F and H of valve 326, to waste through line 348. Simultaneously, dialysate solution in chamber 318 is moved along lines 328 and 344, via ports E' and H' of valve 330 to the solution side of cell 370. From the cell 370 it passes along line 344' through ports G and E of valve 326 to chamber 316 of cylinder 300. Since the volume of chamber 316 is greater than that of chamber 318, blood wastes will be drawn across the membrane 371 to unite with the dialysate solution to fill the greater volume of chamber 316, that quantity of blood wastes being directly related to the cross sectional area of the piston rod and stroke of the piston so that an accurate quantity of blood wastes is drawn on each cycle of the unit.

As the piston 314 reaches its lowermost position, proximity switch 352 is operated to throw the valves 326 and 330 to their positions shown in chain line. At this time, degassed solution enters chamber 318 via ports G' and E' of valve 330 and conduit 328 causing the pistons to begin their upward movement. The blood wastes and dialysate solution contained in chamber 316 will then be moved along conduit 324 and, via ports E and H of valve 326, will be delivered to waste.

At the same time, the degassed dialysate solution previously delivered to chamber 320 will move along conduit 334 and, via ports F' and H' of valve 330 and conduit 344 to be admitted to the solution side of cell 370 from which it will pass along conduit 344' and ports G and F of valve 326 to chamber 322 of cylinder 302. As described hereabove, since chamber 322 is larger than chamber 320 blood wastes will be drawn across membrane 370 to unite with the solution to fill the extra volume of chamber 322.

From the above description it will be apparent that unit A is effective accurately to mix a dialysate solution from water and a concentrate much as in the manner described in application Ser. No. 590,897, filed June 27, 1975. Unit B is effective to degas the solution produced by unit A, and Unit C effects the controlled blood waste withdrawal much as described in co-pending application Ser. No. 590,895, filed June 27, 1975. It is to be appreciated that the units A and C can be modified in any of the manners described in the aforementioned co-pending applications without deviating from the scope of the present invention.

It is also to be appreciated that the piston/cylinder units of the embodiments of FIGS. 2 and 3 utilized for degassing can be mounted in an appropriate pivot arrangement, that pivoting arrangement being substantially as hereinbefore described with reference to the embodiment of FIG. 1.

Figure 4:
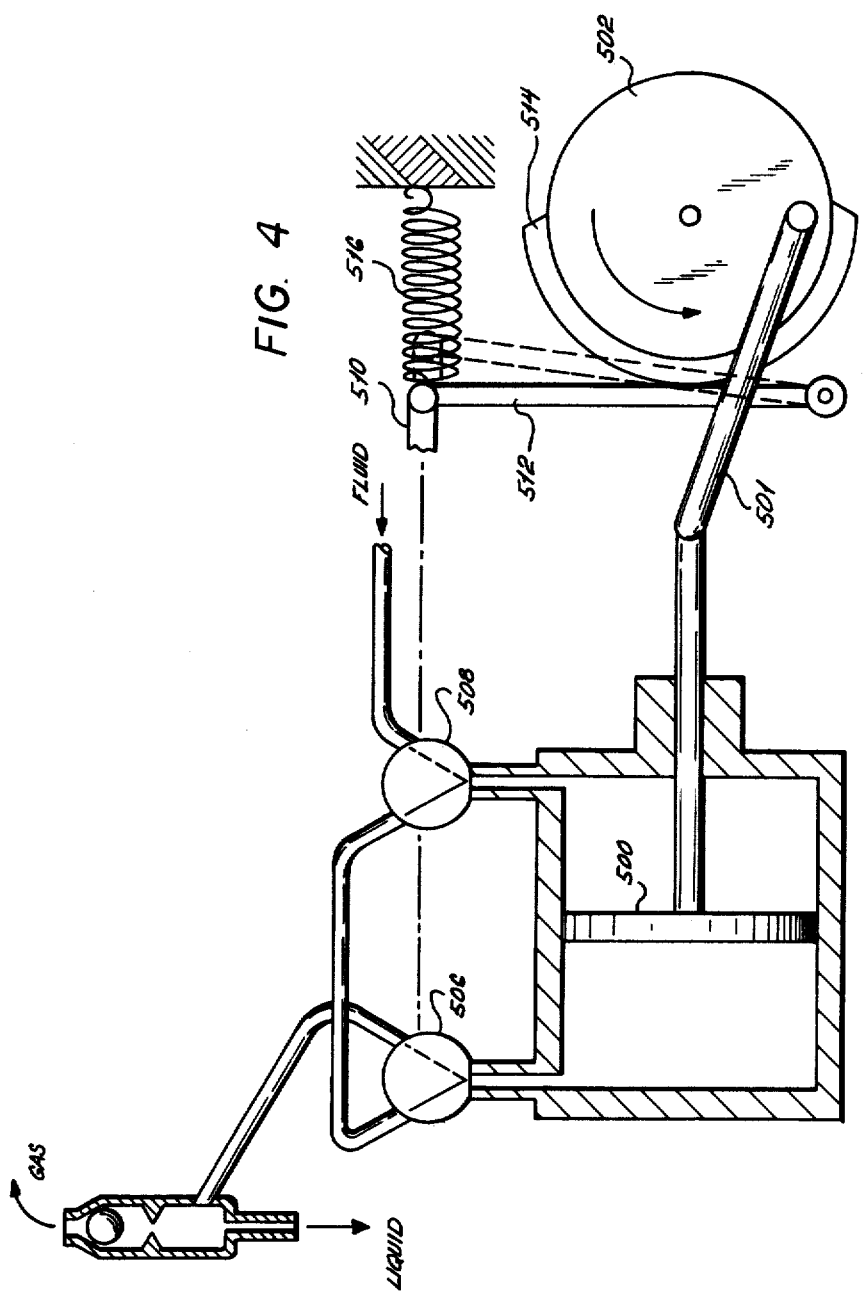
FIG. 4 shows an alternative embodiment of the invention, schematically and partly in section and partly in elevation.

The embodiment of the invention in FIG. 4 is, in operation, largely similar to that of FIG. 1, but in this instance drive is applied to the piston 500 from crank 502 through connecting rod 501 and valves 506 and 508 are operated by a push rod 510 connected to a cam follower lever 512 which cooperates with can 514 on crank 502. The lever 512 is biased into engagement with cam 514 by means of spring 516.

Figure 5:
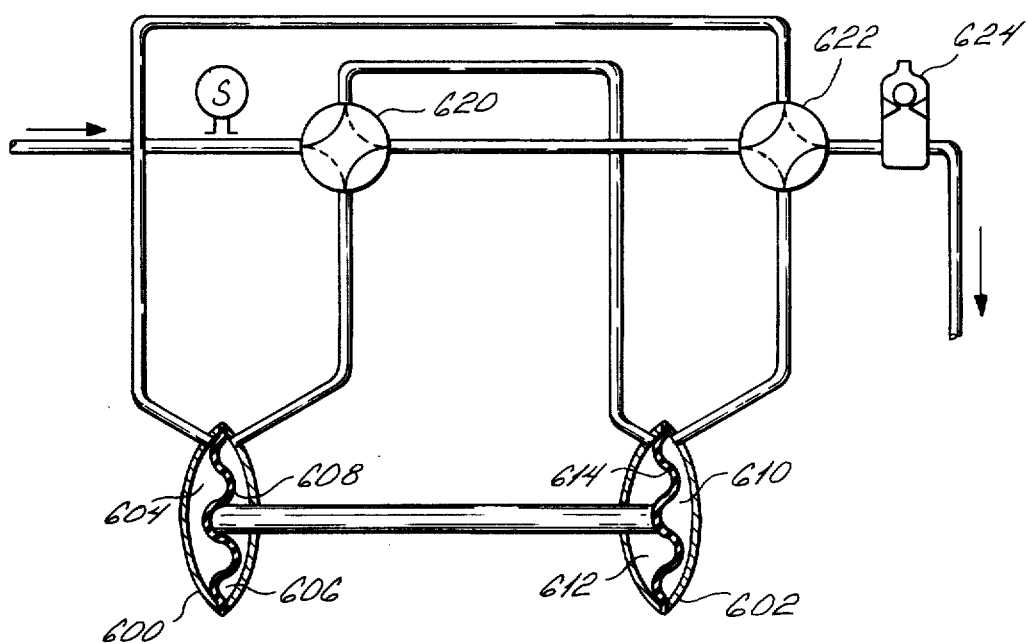
FIG. 5 shows a variation of the duplex system of FIG. 2.

The embodiment of the invention illustrated in FIG. 5 is in many respects similar to that of FIG. 2 and for this reason a detailed description of its operation is omitted. The essential difference resides in the fact that instead of piston/cylinder units, simple receptacles 600 and 602 are provided, receptacle 600 being divided into chambers 604 and 606 by a flexible diaphragm 608 while receptacle 602 is divided into chambers 610 and 612 by a similar flexible diaphragm 614.

Liquid to be subjected to a negative pressure particularly to be degassed, is delivered through valve 620 alternately to chambers 606 and 612 and from chambers 606 and 612 through valves 620 and 622 to chambers 604 and 610, respectively. The resultant liquid and gaseous phases are thereafter passed from chambers 604 and 610 through valve 622 to bubble trap 624 where, if the liquid contains a gas, the gas is separated from the liquid and where, if the liquid does not contain a gas, and vaporization occurs in the chambers 604 and 610, that vapor is re-condensed.

It is to be appreciated that in each of the embodiments here described, the piston/cylinder units can be replaced by the receptacles by the embodiment of FIG. 5.

Each variation of the invention described herein has valves operated by some external agency as, for example, the electrically operated valves of the embodiments of FIG. 1 through 3 and the mechanically operated valves of FIG. 4. It is possible, however, to provide simple check valves and it should be understood that the utilization of such an arrangement is within the scope of the present invention.

The embodiments of the invention illustrated herein have been described with reference to their application in degassing a gas-containing liquid, but it will be understood that this apparatus is effective to expose the fluid passed from one chamber of the cylinder to the other, to a negative pressure. Thus, if the fluid is largely gaseous, the gas will be caused to expand in the larger chamber; if the fluid is a gas-containing liquid then, as described hereabove, the gas will form bubbles and, if the fluid is wholly liquid, the liquid or a part of it will be vaporized and will be condensed as the negative pressure is removed.

What is claimed is:

1. Apparatus for exposing a fluid to a negative pressure comprising a receptacle, a partition reciprocable in the receptacle and dividing the receptacle into two chambers, means for reciprocating said partition, means for reducing the effective volume swept during reciprocation by said partition in one chamber to be lesser than that swept by said partition in the other chamber, an inlet to said one chamber for the admission of a fluid, conduit means connecting said one chamber and said other chamber to provide liquid communication between said chambers, a fluid outlet from said other chamber and interconnected valve means cooperating with said inlet, said outlet and said conduit means to permit controlled reciprocation of said partition within the receptacle, fluid passed through said conduit from said one chamber to said other chamber expanding to occupy the larger volume of said other chamber by the formation of bubbles in said fluid.

2. Apparatus as claimed in claim 1 wherein said means for reducing the effective volume swept by the partition in said one chamber comprises a rod extending from the partition and through said one chamber.

3. Apparatus as claimed in claim 1 wherein said inlet includes means for pressurizing a liquid, said liquid constituting a motive fluid for moving said partition in a direction to expand said one chamber.

4. Apparatus as claimed in claim 1 wherein resilient means are provided to move said partition in a direction to expand said other chamber.

5. Apparatus as claimed in claim 3 wherein resilient means are provided to move said partition in a direction to expand said other chamber.

6. Apparatus as claimed in claim 1 comprising two receptacles, each with a partition and each divided into two chambers by said partition, said partitions being mechanically interconnected and including means for reducing the effective volumes swept by said pistons within one of the chambers of each cylinder to be lesser than those of the other chambers of those cylinders, the lesser volume chamber of one cylinder expanding as the greater volume chamber of the other cylinder expands.

7. Apparatus as claimed in claim 1 wherein said outlet communicates with said other chamber in an upper region of that chamber.

8. Apparatus as claimed in claim 7 wherein said receptacle comprises a cylinder and said partition, a piston, said cylinder being disposed generally horizontally.

9. Apparatus as claimed in claim 8 wherein said cylinder is mounted for pivoting movement in a vertical plane.

10. Apparatus as claimed in claim 1 wherein means are provided for connecting said outlet to a device for removing said bubbles.

11. Apparatus as claimed in claim 1 wherein said inlet includes means for mixing a solution.

12. Apparatus as claimed in claim 11 wherein said means for mixing a solution comprises a receptacle with a partition dividing the receptacle thereof into two chambers, means for reciprocating said partition within said receptacle, means reducing the effective volume swept by said partition during reciprocation in one chamber to be lesser than that swept by said partition in the other chamber, first conduit means constituting an inlet for a first fluid to said one chamber and connectable to a source of said first fluid, second conduit means connecting said one chamber to said other chamber, third conduit means connected to said other chamber and constituting an outlet for mixed fluids, fourth conduit means constituting an inlet for a second fluid and connectable between a source of a second fluid and said mixing apparatus to cause said second fluid to be added to the first fluid in an amount directly related to the difference in effective volumes of said chambers swept by said piston of said unit and interconnected valve means cooperating in said conduit means to permit controlled reciprocation of said piston of said unit in said cylinder.

13. Apparatus as claimed in claim 1 wherein a liquid outlet of said device for removing said gaseous phase is connected to dialysis apparatus.

14. Apparatus as claimed in claim 13 wherein said dialysis apparatus comprises a dialyser cell having a membrane dividing said cell into a blood side and a solution side and means for delivering dialysate solution to said solution side of said cell, said means for delivering said solution comprising a hydraulic circuit including a receptacle, a partition reciprocable in said receptacle and dividing said receptacle into two chambers, means reducing the effective volume swept by the partition in one chamber to be lesser than the volume swept by the partition in the other chamber, first conduit means constituting an inlet for the dialysate solution to said one chamber and connectable to a source of the dialysate solution, second conduit means connecting said one chamber to said other chamber and including the dialysis cell, third conduit means connected to the other chamber and constituting an outlet for dialysate mixed with blood wastes, whereby the wastes are caused to be drawn across the membrane in a volume directly related to the difference in effective volume swept by the piston in said cylinder.

15. A hemodialysis system comprising means for preparing a dialysate solution and apparatus for degassing that solution comprising a receptacle, a partition reciprocable in the receptacle and dividing the receptacle into two chambers, means reducing the effective volume swept by said partition, in one chamber to be lesser than that swept by said partition in the other chamber, an inlet to said one chamber for the admission of said solution, conduit means connecting said one chamber and said other chamber, an outlet from said other chamber and interconnected valve means cooperating with said inlet, said outlet and said conduit means to permit controlled reciprocation of said partition within the receptacle, gas entrained in said solution passed from said one chamber to said other chamber forming bubbles to occupy the larger volume of said other chamber and means connecting said outlet to a device for separating said gas the liquid, a liquid outlet from said device being connectable to a dialysis cell.

16. Apparatus as claimed in claim 6 wherein said receptacles are aligned and said partitions are coupled by a rod, said rod extending through adjacent walls of said receptacles and constituting said means for reducing the effective volume of said chambers.

17. Apparatus as claimed in claim 10 wherein said device for removing said bubbles of said fluid comprises a bubble trap having a gas outlet and a liquid outlet.

18. The method of exposing a fluid to a negative pressure within a closed system which comprises delivering a determined volume of that fluid to a first chamber, making a connection from that first chamber to a second, larger chamber, causing said determined volume to be transferred and expanded, through said connection, to fill said second chamber.

19. A method of degassing a liquid in a closed system which comprises delivering a determined volume of said liquid to a first chamber of a closed system, making a connection from that first chamber to a second larger chamber of the system, causing said determined volume to be transferred, through said connection, to said second chamber, to expand in said chamber and release a gaseous phase and thereafter, passing said liquid and gaseous phases from said second chamber to separating means.

20. Apparatus as claimed in claim 11 wherein said means for mixing a solution comprises a first receiving chamber receiving a predetermined volume of a primary liquid, a second receiving chamber, means connecting said chambers, means transporting liquid from said first chamber to said second chamber through said connecting means, inlet means for a secondary liquid communicating with said connecting means and means rendering the volume of said second chamber greater than the predetermined volume of primary liquid whereby secondary liquid is delivered through said connecting means to fill, with said primary liquid, said second chamber.

21. Apparatus as claimed in claim 13 wherein said dialysis apparatus comprises a dialyzer cell having blood and dialysate solution sides, a first receiving chamber receiving a determined volume a dialysate solution from said device for removing said gaseous phases, a second receiving chamber, means connecting said chambers to said dialysate solution side of said cell, means transporting liquid from said first chamber to said second chamber through said connecting means and means rendering the volume of said second chamber greater than said predetermined volume of dialysate solution whereby blood wastes are drawn across said cell to fill, with said solution, said second chamber.

22. Apparatus as claimed in claim 1 wherein said receptacle comprises a cylinder and said partition a piston reciprocable in the cylinder.

23. Apparatus as claimed in claim 1 wherein said partition comprises a flexible diaphragm.

* * * * *